United States Patent
Gibson et al.

(10) Patent No.: US 12,112,844 B2
(45) Date of Patent: Oct. 8, 2024

(54) MACHINE LEARNING FOR AUTOMATIC DETECTION OF INTRACRANIAL HEMORRHAGES WITH UNCERTAINTY MEASURES FROM MEDICAL IMAGES

(71) Applicant: SIEMENS HEALTHINEERS AG, Forchheim (DE)

(72) Inventors: Eli Gibson, Plainsboro, NJ (US); Bogdan Georgescu, Princeton, NJ (US); Pascal Ceccaldi, New York, NY (US); Youngjin Yoo, Princeton, NJ (US); Jyotipriya Das, Plainsboro, NJ (US); Thomas Re, New York, NY (US); Eva Eibenberger, Nuremberg (DE); Andrei Chekkoury, Erlangen (DE); Barbara Brehm, Forchheim (DE); Thomas Flohr, Uehlfeld (DE); Dorin Comaniciu, Princeton, NJ (US); Pierre-Hugo Trigan, Saint Martin du Manoir (FR)

(73) Assignee: Siemens Healthineers AG, Forchheim (DE)

( * ) Notice: Subject to any disclaimer, the term of this patent is extended or adjusted under 35 U.S.C. 154(b) by 468 days.

(21) Appl. No.: 17/249,783

(22) Filed: Mar. 12, 2021

(65) Prior Publication Data
US 2022/0293247 A1  Sep. 15, 2022

(51) Int. Cl.
*G16H 30/40* (2018.01)
*G06N 20/00* (2019.01)
*G16H 50/20* (2018.01)

(52) U.S. Cl.
CPC ............. *G16H 30/40* (2018.01); *G06N 20/00* (2019.01); *G16H 50/20* (2018.01)

(58) Field of Classification Search
CPC ........ G16H 30/40; G16H 50/20; G16H 50/30; G16H 40/20; G16H 30/00; G06T 11/003;
(Continued)

(56) References Cited

U.S. PATENT DOCUMENTS 10,916,341 B2 * 2/2021 Stoval, III ............. G16H 50/30
11,488,067 B2 * 11/2022 Luong .................... G06N 3/084
(Continued)

FOREIGN PATENT DOCUMENTS

CN       111368849 A     7/2020
WO    2019232027 A1    12/2019

OTHER PUBLICATIONS

On Calibration of Modern Neural Networks (Year: 2017).*
(Continued)

*Primary Examiner* — Amandeep Saini
*Assistant Examiner* — Mehrazul Islam

(57) ABSTRACT

Systems and method for performing a medical imaging analysis task for making a clinical decision are provided. One or more input medical images of a patient are received. A medical imaging analysis task is performed from the one or more input medical images using a machine learning based network. The machine learning based network generates a probability score associated with the medical imaging analysis task. An uncertainty measure associated with the probability score is determined. A clinical decision is made based on the probability score and the uncertainty measure.

15 Claims, 6 Drawing Sheets

(58) Field of Classification Search
CPC ..... A61B 6/5211; A61B 5/02042; A61B 6/03; A61B 8/0808; G06N 3/084; G06N 20/00; G01V 2210/667; G06F 30/27; H03M 13/1125

See application file for complete search history.

(56) References Cited

U.S. PATENT DOCUMENTS

| | | | | |
|---|---|---|---|---|
| 2015/0141859 | A1* | 5/2015 | Sandler | G06F 17/18 600/516 |
| 2016/0267673 | A1* | 9/2016 | Grbic | G16H 30/40 |
| 2019/0156212 | A1* | 5/2019 | Bottaro | G06F 16/951 |
| 2019/0339291 | A1 | 11/2019 | Edmonds et al. | |
| 2020/0320354 | A1 | 10/2020 | Ghesu et al. | |
| 2021/0005320 | A1* | 1/2021 | Lötjönen | G16H 70/60 |
| 2021/0093278 | A1* | 4/2021 | Kalafut | A61B 6/501 |
| 2021/0104321 | A1* | 4/2021 | Lipsky | G16H 70/40 |
| 2021/0217167 | A1* | 7/2021 | Lee | G16H 30/20 |
| 2022/0180516 | A1* | 6/2022 | Mavroeidis | G06T 7/70 |
| 2022/0285024 | A1* | 9/2022 | Pezzotti | G16H 50/20 |

OTHER PUBLICATIONS

A nonparametric Bayesian method of translating machine learning scores to probabilities in clinical decision support (Year: 2017).*
Advanced machine learning in action: identification of intracranial hemorrhage on computed tomography scans of the head with clinical workflow integration (Year: 2018).*
Beta Distribution-Based Cross-Entropy for Feature Selection (Year: 2019).*
Extended European Search Report (EESR) mailed Aug. 4, 2022 in corresponding European Patent Application No. 22161645.1.
Nawabi Jawed et al: "Imaging-Based Outcome Prediction of Acute Intracerebral Hemorrhage"; Translational Stroke Research; Springer; vol. 12; No. 6; pp. 958-967.
Li Lu et al: "Deep Learning for Hemorrhagic Lesion Detection and Segmentation on Brain CT Images"; IEEE Journal of Biomedical and Health Informatics; vol. 25; No. 5; pp. 1646-1659.
Salmela et al., "ACR Appropriateness Criteria Cerebrovascular Disease," 2017, Journal of the American College of Radiology, vol. 14, Issue 5, pp. S34-S61.
Shetty et al., "ACR Appropriateness Criteria Head Trauma," 2016, Journal of the American College of Radiology, vol. 13, Issue 6, pp. 668-679.
Asch et al., "Incidence, case fatality, and functional outcome of intracerebral haemorrhage over time, according to age, sex, and ethnic origin: a systematic review and meta-analysis," 2010, The Lancet, Neurology, vol. 9, Issue 2, pp. 167-176.
Wardlaw et al., "Recombinant tissue plasminogen activator for acute ischaemic stroke: an updated systematic review and meta-analysis," 2012, The Lancet, vol. 379, Issue 9834, pp. 2364-2372.
National Institution for Health and Care Excellence, "Head Injury: Assessment and Early Management," 2014, NICE Clinical guideline (CG176), 60 pgs.
Bershad et al., "Multidisciplinary Protocol for Rapid Head Computed Tomography Turnaround Time in Acute Stroke Patients," 2015, Journal of Stroke and Cerebrovascular Diseases vol. 24, Issue 6, pp. 1256-1261.
American Heart Association/American Stroke Association; Stroke Fact Sheet; Feb. 2017; Accessed Sep. 22, 2020.
Yaniv et al., "Deep Learning Algorithm for Optimizing Critical Findings Report Turnaround Time," 2018, SIIM (Society for Imaging Informatics in Medicine) Annual Meeting, 3 pgs.
Arbabshirani et al., "Advanced machine learning in action: identification of intracranial hemorrhage on computed tomography scans of the head with clinical workflow integration," 2018, NPJ Digital Medicine, vol. 1, No. 9, pp. 1-7.
Kuo et al., "Expert-level detection of acute intracranial hemorrhage on head computed tomography using deep learning," 2019, Proceedings of the National Academy of Sciences, vol. 116, No. 45, pp. 22737-22745.
Flanders et al., "Construction of a Machine Learning Dataset through Collaboration: The RSNA 2019 Brain CT Hemorrhage Challenge," 2020, Radiology: Artificial Intelligence, vol. 2, No. 3, e190211, 7 pgs.
Ghesu et al., "Multi-Scale Deep Reinforcement Learning for Real-Time 3D-Landmark Detection in CT Scans," 2017, IEEE Transactions on Pattern Snalysis and Machine Intelligence, vol. 41, No. 1, pp. 176-189.
Yang et al., "Automatic liver segmentation using an adversarial image-to-image network," 2017, In International Conference on Medical Image Computing and Computer-Assisted Intervention, Part III, LNCS 10435, pp. 507-515.
Kaivanto, "Maximization of the sum of sensitivity and specificity as a diagnostic cutpoint criterion," 2008, Journal of Clinical Epidemiology, No. 61, pp. 517-518.
Guo et al., "On Calibration of Modern Neural Networks," 2017, Proceedings of Machine Learning Research, vol. 70, pp. 1321-1330.
Harang et al., "Towards Principled Uncertainty Estimation for Deep Neural Networks," 2018, https://arxiv.org/pdf/1810.12278.pdf., 12 pgs.
Hein et al., "Why ReLU Networks Yield High-Confidence Predictions Far Away From the Training Data and How to Mitigate the Problem," 2019, Proceedings of the IEEE/CVF Conference on Computer Vision and Pattern Recognition (CVPR), pp. 41-50.
Ghesu et al., "Quantifying and Leveraging Classification Uncertainty for Chest Radiograph Assessment," 2019, In International Conference on Medical Image Computing and Computer-Assisted Intervention, LNCS 11769, pp. 676-684.
Rau et al., "Concurrent Types of Intracranial Hemorrhage are Associated with a Higher Mortality Rate in Adult Patients with Traumatic Subarachnoid Hemorrhage: A Cross-Sectional Retrospective Study," 2019, International Journal of Environmental Research and Public Health, vol. 16, No. 23, 4787, 9 pgs.
Broderick et al., "Volume of intracerebral hemorrhage. A powerful and easy-to-use predictor of 30-day mortality," 1993, Stroke, vol. 24, pp. 987-993.
Davis et al., "Hematoma growth is a determinant of mortality and poor outcome after intracerebral hemorrhage," 2006, Neurology, vol. 66, No. 8, pp. 1175-1181.
Rodriguez-Luna et al., "Magnitude of Hematoma Volume Measurement Error in Intracerebral Hemorrhage," 2016, Stroke, vol. 47, No. 4, pp. 1124-1126.
Lebovitz, "Diagnostic Doubt and Artificial Intelligence: An Inductive Field Study of Radiology Work," 2019, ICIS 2019 Proceedings, vol. 11, 18 pgs.
U.S. Appl. No. 17/072,424, filed Oct. 16, 2020.

\* cited by examiner

MACHINE LEARNING FOR AUTOMATIC DETECTION OF INTRACRANIAL HEMORRHAGES WITH UNCERTAINTY MEASURES FROM MEDICAL IMAGES

TECHNICAL FIELD

The present invention relates generally to the detection of intracranial hemorrhages, and in particular to machine learning for automatic detection of intracranial hemorrhages with uncertainty measures from CT (computed tomography) images.

BACKGROUND

Non-contrast CT (computed tomography) imaging is the most common form of medical imaging for the evaluation of urgent and emergent neurological conditions. In the current clinical practice, non-contrast CT imaging is the standard of care for the assessment of acute strokes and head trauma, and is particularly useful for detecting acute ICH (intracranial hemorrhage). Minimizing time-to-interpretation of CT imaging and time-to-intervention is important for patient outcome.

Recently, machine learning systems have been proposed for automatically assessing CT images for ICH and other medical conditions. However, such machine learning systems are not able to explain the results of the assessment. While machine learning systems often generate a score representing the result of the assessment, such score itself may be unreliable. Accordingly, clinicians are not able to rely on the results of the assessment from such machine learning systems and thus are not able to reliably incorporate such machine learning systems in clinical workflows.

BRIEF SUMMARY OF THE INVENTION

In accordance with one or more embodiments, systems and method for performing a medical imaging analysis task for making a clinical decision are provided. One or more input medical images of a patient are received. A medical imaging analysis task is performed from the one or more input medical images using a machine learning based network. The machine learning based network generates a probability score associated with the medical imaging analysis task. An uncertainty measure associated with the probability score is determined. A clinical decision is made based on the probability score and the uncertainty measure.

In one embodiment, the uncertainty measure is determined by applying a calibration function to the probability score and calculating an entropy of the probability score based on results of the applied calibration function. In another embodiment, the machine learning based network generates parameters of a beta distribution of scores and the uncertainty measure is determined by calculating an entropy of the beta distribution based on the parameters and combining the entropy of the beta distribution to an entropy of the probability score.

In one embodiment, making a clinical decision comprises stratifying the patient into one of a plurality of patient groups based on the probability score and the uncertainty measure. Where the medical imaging analysis task comprises detection of an intracranial hemorrhage of the patient, the plurality of patient groups may comprise a high confidence positive detection patient group, a high confidence negative detection patient group, and a low confidence patient group. In another embodiment, making a clinical decision comprises determining whether to treat the patient based on the probability score and the uncertainty measure. In another embodiment, making a clinical decision comprises determining whether to perform a clinical test on the patient based on the probability score and the uncertainty measure. In another embodiment, making a clinical decision comprises prioritizing a worklist of a radiologist based on the probability score and the uncertainty measure.

In one embodiment, the medical imaging analysis task comprises at least one of detection, subtyping, or segmentation of an intracranial hemorrhage of the patient.

These and other advantages of the invention will be apparent to those of ordinary skill in the art by reference to the following detailed description and the accompanying drawings.

DETAILED DESCRIPTION

The present invention generally relates to methods and systems for machine learning for automatic detection of intracranial hemorrhage with uncertainty measures from CT (computed tomography) images. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for the automatic detection, subtyping, and segmentation of ICH (intracranial hemorrhage) on non-contract head CT images using a machine learning based network. The machine learning based network generates probability scores (e.g., classification scores) for the detection and subtyping of ICH. In accordance with embodiments described herein, uncertainty measures associated with the probability scores are determined. Advantageously, the uncertainty measures associated with the probability scores reliably inform clinicians of the uncertainty associated with the detection, subtyping, and segmentation of ICH, thereby enabling reliable clinical decision making based on the probability scores and uncertainty measures.

Figure 1:
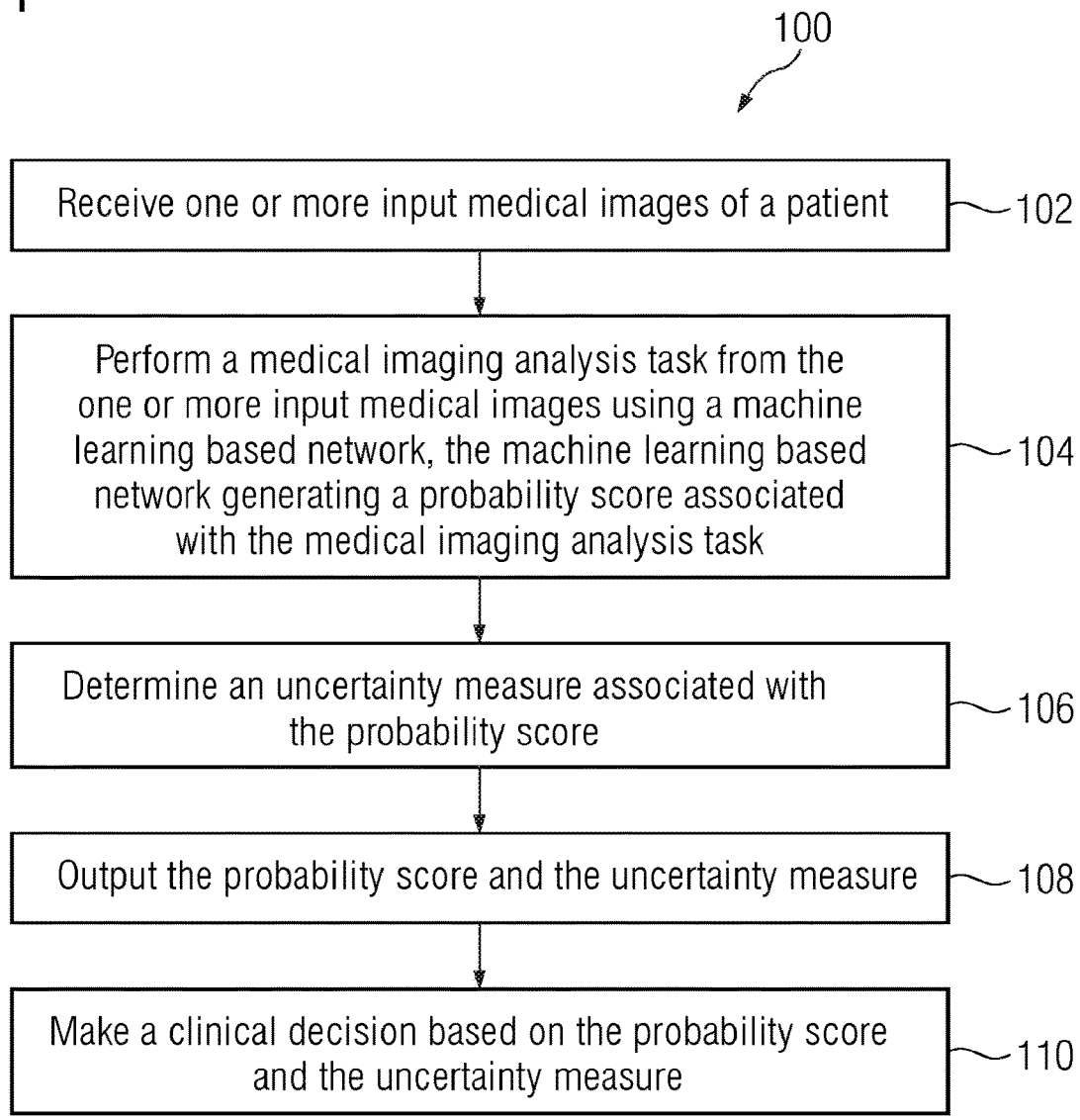
FIG. 1 shows a method for clinical decision making based on an automatically performed medical imaging analysis task, in accordance with one or more embodiments.

FIG. 1 shows a method 100 for clinical decision making based on an automatically performed medical imaging analysis task, in accordance with one or more embodiments. The steps of method 100 may be performed by one or more suitable computing devices, such as, e.g., computer 602 of FIG. 6.

At step 102, one or more input medical images of a patient are received. The one or more input medical images may be of any anatomical object of interest of the patient, such as, e.g., organs, bones, lesions, etc. In one example, the one or more input medical images are of a head of the patient.

In one embodiment, the one or more input medical images comprise CT images, such as, e.g., non-contrast CT images. However, the one or more input medical images may comprise any other suitable modality, such as, e.g., MRI (magnetic resonance imaging), ultrasound, x-ray, or any other medical imaging modality or combinations of medical imaging modalities. The one or more input medical images may comprise 2D (two dimensional) images and/or 3D (three dimensional) volumes, and may comprise a single input medical image or a plurality of input medical images. In one embodiment, the one or more input medical images comprises 2.5D (2D plus time) images. The one or more input medical images may be received directly from an image acquisition device, such as, e.g., a CT scanner, as the medical images are acquired, or can be received by loading previously acquired medical images from a storage or memory of a computer system or receiving medical images that have been transmitted from a remote computer system.

At step 104, a medical imaging analysis task is performed from the one or more input medical images using a machine learning based network. The machine learning based network generates a probability score associated with the medical imaging analysis task. The medical imaging analysis task may be any task or tasks performed on one or more medical images using any suitable machine learning based network. For example, the medical imaging analysis task may comprise detection, classification, segmentation, etc. The probability score may represent a likelihood for a particular result of the medical imaging analysis task. In one example, where the medical imaging analysis task is classification, the probability score may be a classification score (e.g., 0.8) representing a likelihood for a particular classification.

Figure 2:
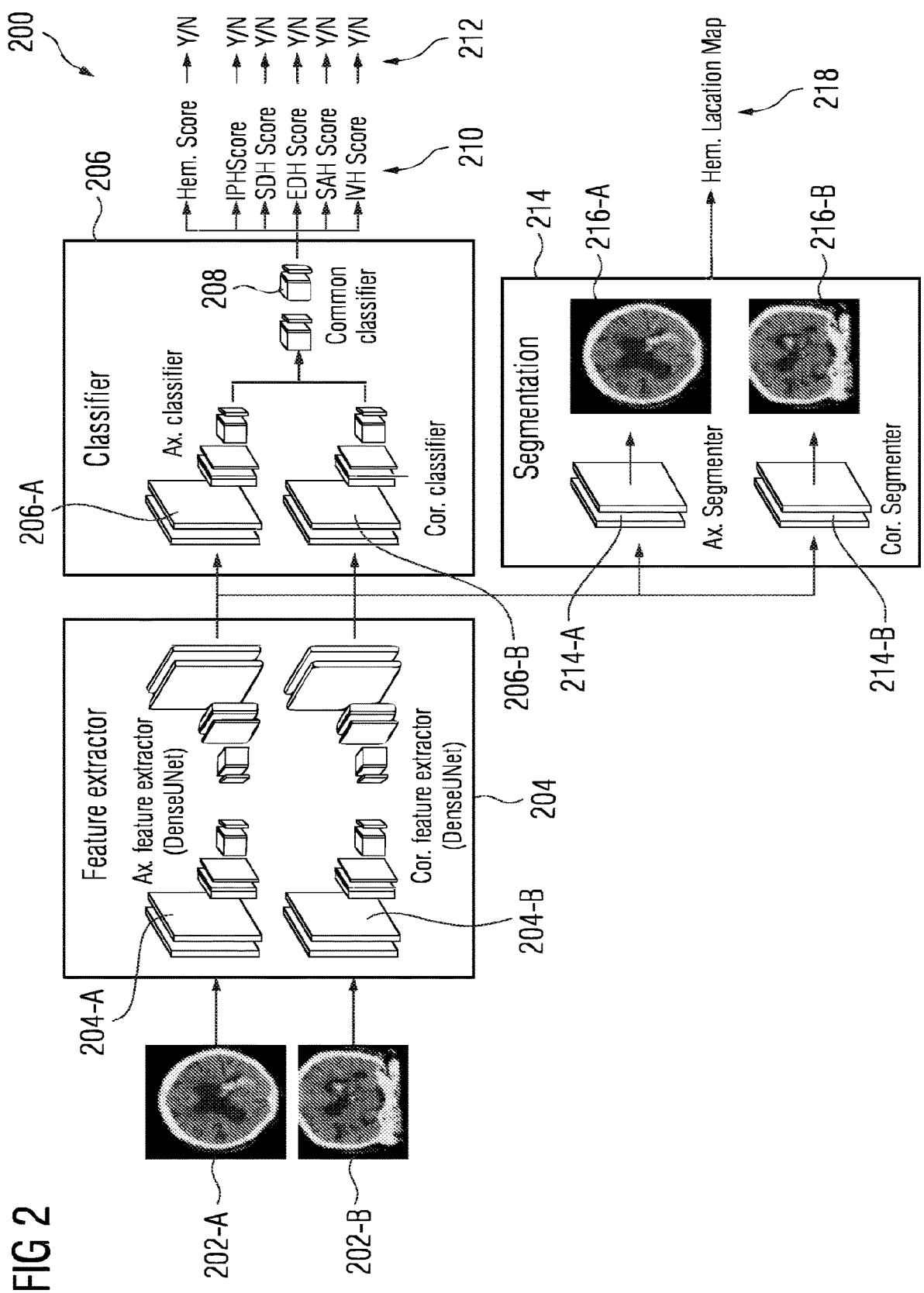
FIG. 2 shows a network architecture of a deep learning network trained for detecting, segmenting, and subtyping intracranial hemorrhage, in accordance with one or more embodiments.

In one embodiment, the medical imaging analysis task comprises detecting, segmenting, and subtyping ICH on non-contrast CT input medical images of a head of the patient. FIG. 2 shows a network architecture 200 of a deep learning network trained for detecting, segmenting, and subtyping ICH, in accordance with one or more embodiments. Network architecture 200 comprises three blocks: 1) a feature extractor block 204 comprising axial feature extractor 204-A and coronal feature extractor 204-B, 2) a classifier block 206 comprising axial classifier 206-A, coronal classifier 206-B, and a common classifier 208, and 3) a segmentation block 214 comprising axial segmenter 214-A and coronal segmenter 214-B. Axial feature extractor 204-A and coronal feature extractor 204-B respectively extract features from axial CT input medical image 202-A and coronal CT input medical image 202-B. The extracted features are respectively input into axial classifier 206-A and coronal classifier 206-B and axial segmenter 214-A and coronal segmenter 214-B. Results of axial classifier 206-A and coronal classifier 206-B are combined by common classifier 208 to generate probability scores 210. Probability scores 210 include a hemorrhage score representing the probability of a detection of ICH as well as an IPH (intraparenchymal hemorrhage) score, SDH (subdural hemorrhage) score, EDH (extradural hemorrhage) score, SAH (subarachnoid hemorrhage) score, and IVH (intraventricular hemorrhage) score representing the probability of a subtype of the ICH. Probability scores 210 may be converted to positive or negative (i.e., yes or no) results 212, e.g., by comparing the probability scores 210 to one or more thresholds. Axial segmenter 214-A and coronal segmenter 214-B respectively generate an axial segmentation map 216-A and a coronal segmentation map 216-B, which are combined to generate a hemorrhage location map 218.

The deep learning network of network architecture 200 is trained during a prior offline or training stage using training data. The network weights may be optimized in two phases: the feature extractor networks and segmenter networks may be first optimized alone minimizing voxel-wise binary cross-entropy segmentation loss with respect to manual segmentation, then all networks may be optimized together minimizing the linear combination of the segmentation losses and the study-level sigmoid binary cross-entropy classification losses with respect to six manual labels for ICH and the IPH, SDH, EDH, SAH, and IVH subtypes. Once trained, the trained deep learning network may be applied during an online or testing stage (e.g., at step 104 of FIG. 4).

Figure 3:
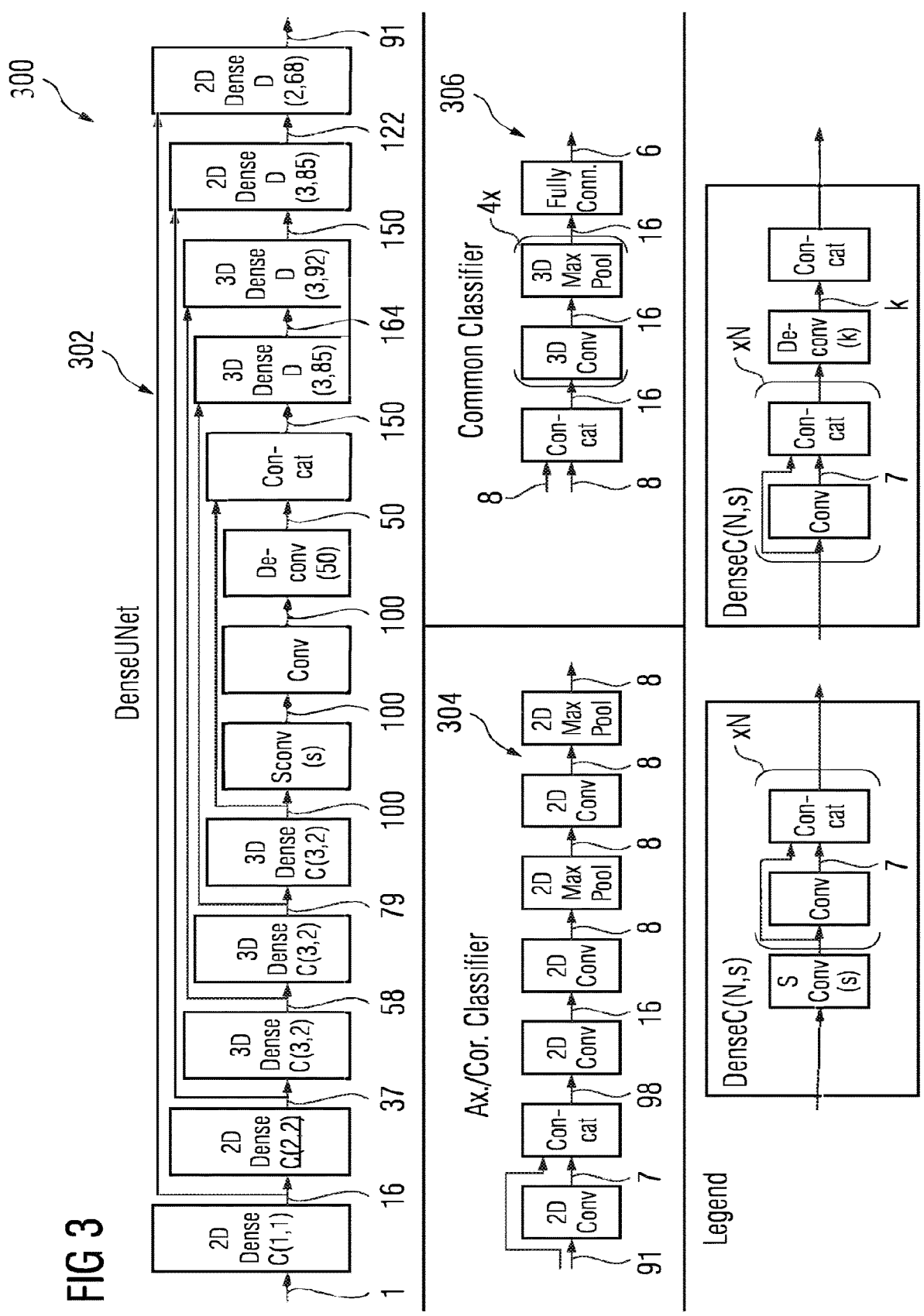
FIG. 3 shows network architecture details for various networks in the network architecture of FIG. 2, in accordance with one or more embodiments.

FIG. 3 shows network architecture details 300 for various networks in network architecture 200 of FIG. 2, in accordance with one or more embodiments. Network architecture details 300 of FIG. 3 will be described with continued reference to network architecture 200 of FIG. 2. Axial feature extractor 204-A and coronal feature extractor 204-B may be implemented as DenseUNet 302. Axial classifier 206-A and coronal classifier 206-B may be implemented as axial/coronal classifier 304. Common classifier 208 may be implemented as common classifier 306. The annotated arrows in network architecture details 300 show the number of channels in each feature map. Stride convolutions (SConv) with stride 2 result in halving the feature map size in-plane (for 2D) or in all dimension (for 3D). Deconvolutions (Deconv) result in doubling the feature map size. All convolutions use kernels of size 3. The axial CT input medical image 202-A and coronal CT input medical image 202-B were preprocessed to have voxel spacings of 1 mm×1 mm×4 mm and 1 mm×4 mm×1 mm and were rescaled so that the range 0-1 maps to a wide window with window level WL=55 HU (Hounsfield units) and window width WW=200 HU.

Returning to FIG. 1, at step 106, an uncertainty measure associated with the probability score is determined. The uncertainty measure may be any suitable measure representing uncertainty associated with the probability score. For example, the uncertainty measure may represent an error associated with the probability score. In this example, where the probability score is 0.8, the uncertainty measure may be plus/mins 0.1.

In one embodiment, the uncertainty measure is a calibrated-classifier uncertainty measure. The calibrated-classifier uncertainty measure considers the entropy of the probability score determined by the machine learning based network. A calibration function is selected from a family of monotonically increasing functions with three fixed points: <0,0>, <d,0.5>, and <1,1>, where d is a user selected decision threshold. All such calibration functions have the property $H(C_a(p=d))$, where H is the entropy and p is the probability score (determined at step 104 of FIG. 1). That is, probability scores that are exactly at the selected decision threshold are considered totally uncertain. In one embodiment, the calibration function Ca(p) is applied to the probability score to map a specified operating point threshold t to 0.5 as follows:

$$Ca(p) = \frac{-1}{p^{\log_2(t)}}$$

Other calibration functions may also be applied, such as, e.g., the cumulative distribution function of a Kumaraswamy distribution. The entropy of the probability score is then calculated based on results of the applied calibration function as a calibrated-classifier uncertainty measure as follows:

$$H(Ca(p))=-Ca(p)\log_2(Ca(p))-(1-Ca(p))\log_2(1-Ca(p))$$

In one embodiment, the uncertainty measure is a Dempster-Shafer uncertainty measure, which considers additional uncertainty estimated during training. In this embodiment, the machine learning based network generates distribution parameters of a Beta distribution of scores, where the mean is the probability score and a narrower distribution indicates a higher confidence. The distribution parameters of the beta distribution of scores may be belief masses representing evidence in the input medical images for a classification label. For example, the distribution parameters of the beta distribution of scores may include α representing evidence of a positive classification label and β representing evidence of a negative classification label. The entropy of the beta distribution around an operating point threshold is calculated based on the distribution parameters as a measure of additional uncertainty. The entropy of the beta distribution is combined with (e.g., added to) the calibrated-classifier uncertainty measure (i.e., the entropy of the probability score) to determine the Dempster-Shafer uncertainty measure.

In another embodiment, instead of distribution parameters of a Beta distribution, the machine learning based network generates distribution parameters of a Kumaraswamy distribution, the entropy of the Kumaraswamy distribution around an operating point threshold is calculated based on the distribution parameters, and the entropy of the Kumaraswamy distribution is combined with the calibrated-classifier uncertainty measure to determine the Dempster-Shafer uncertainty measure. Calculation of Dempster-Shafer uncertainty measures is further described in U.S. Patent Publication No. 2020/0320354, filed Sep. 5, 2019, and U.S. Patent Publication No. 2022/0028063, filed Oct. 16, 2020, the disclosures of which are incorporated herein by reference in their entirety.

To generate the parameters of a beta distribution of scores, the machine learning based network may be trained using a typical binary-cross entropy loss, and then the final layers of the network may be finetuned with a second loss that takes the form of:

$$\underbrace{\mathcal{L}}_{\text{Likelihood}} = \underbrace{\sum_{k=1}^{N} \int \|y_k - p_k\|^2 \frac{\Gamma(\alpha+\beta)}{\Gamma(\alpha)\Gamma(\beta)} p_k^{\alpha-1}(1-p_k)^{\beta-1} dp_k}_{\text{Bayes risk with beta prior}} + \underbrace{\lambda KL(f(\widehat{p_k}; \widetilde{\alpha_k}, \widetilde{\beta_k}) | f(\widehat{p_k}; <1, 1>))}_{\text{Regularization}}$$

where the first term measures the data fitting cost and the second term is a regularization term for inconclusive samples. $y_k$ represents the ground truth label, $p_k$ represents the prediction for the $k^{th}$ of N training cases, Γ is the Gamma function parameterized by α and β, and KL is the Kullback-Leibler divergence between the beta distribution prior term and the beta distribution with total uncertainty (that is α=β=1). A calibration function that measures the entropy of the probability score exceeding a calibrated operating point may be applied, which can be computed from the cumulative distribution function of the parametrized beta distribution:

$$p_{ds}=B(x;\alpha,\beta)/\beta(\alpha,\beta)$$

$$E_{ds}=p_{ds}\log(p_{ds})+(1-p_{ds})\log(1-p_{ds})$$

where B is the beta function, x is the chosen operating point, $p_{ds}$ is the probability score, and $E_{ds}$ is the entropy of the probability score.

At step 108, the probability score and the uncertainty measure are output. For example, the probability score and the uncertainty measure can be output by displaying the probability score and the uncertainty measure on a display device of a computer system, storing the probability score and the uncertainty measure on a memory or storage of a computer system, or by transmitting the probability score and the uncertainty measure to a remote computer system. In one embodiment, the probability score and the uncertainty measure may be output to a system for, e.g., automatic clinical decision making or further processing of the patient.

At step 110, a clinical decision is made based on the probability score and the uncertainty measure. In one embodiment, the clinical decision comprises stratifying the patient into one of a plurality of patient groups, e.g., to separate patients into a three-way triage of a high confidence positive classification (e.g., positive detection of ICH) patient group, a high confidence negative classification (e.g., negative detection of ICH) patient group, and a low confidence patient group. In another embodiment, the clinical decision comprises determining whether to treat a patient. In another embodiment, the clinical decision comprises determining whether to perform a clinical test on the patient. In another embodiment, the clinical decision comprises prioritizing a worklist of a radiologist based on the probability score and the uncertainty measure. The clinical decision may be made based on one or more thresholds. The clinical decision may be any other suitable clinical decision.

Embodiments described herein provide for an uncertainty measure associated with the probability score determined by the machine learning based network. While the probability score determined by the machine learning based network may represent a likelihood for the medical imaging analysis task, the probability score determined by the machine learning based network may involve a level of uncertainty. Advantageously, the uncertainty measure calculated in accordance with embodiments described herein provides for a level of uncertainty for the probability score, enabling results of the medical imaging analysis task to be reliably used for clinical decision making.

Embodiments described herein were experimentally validated on 46,057 non-contrast head CT images acquired from ten center using scanners from various manufacturers. 25,946 of those images were acquired from seven "seen" centers to develop and optimize the system, including iterative architecture selection, parameter tuning, and training. 400 of those images were acquired from 3 "unseen" centers from the RSNA (Radiological Society of North America) ICH challenge training dataset to calibrate the system. 2,947 of the images from "seen" centers with no patient overlap and 16,764 of the images from the RSNA ICH challenge training dataset were then used to measure the performance of the system.

Study level labels for ICH and subtypes were generated in one of three ways. For the RSNA dataset, labels were provided with the dataset, which were assigned at the slice level by one of sixty radiologists reviewing the images. For the images from the seen centers, in 6,649 images across three centers, study level labels were provided by the contributing centers based on review by a center radiologist of the images or the radiological reports. In 22,244 images across four centers, radiological reports were provided by the contributing center and were manually transcribed by a team of trained annotators (with at least forty hours of training in CT hemorrhage annotation supervised by a radiologist) and reviewed by a technologist (with a Bachelor's degree in radiology and medical imaging technologist training with one year of training in neuroimaging) and one of three radiologists (with at least five years of experience). For a subset of 3,278 of ICH-positive cases, acute/subacute ICH was manually segmented and reviewed by the same team.

Probability scores and uncertainty measures were determined in accordance with embodiments described herein. The uncertainty measures were evaluated by measuring ROC (receiver-operating-characteristics) metrics (e.g., AUC (area under curve), sensitivity, and specificity). The uncertainty measures were further evaluated by modeling the average RTAT (report turn-around time) for positive cases comparing a three-way prioritized worklist (e.g., low uncertainty (i.e., high confidence) positive cases, low uncertainty negative cases, and high uncertainty cases) to a first-in-first-out worklist. Specifically, a radiologist reading a fixed worklist in a prioritized or non-prioritized sequence was modelled with two simplifying assumptions: 1) within each priority level, the true hemorrhage cases are positioned randomly in the queue, and 2) each case takes a fixed time T to complete independent of hemorrhage status and priority level. In this model, the average RTAT t can be written as follows:

$$t = T(n_1(p_1 + 2p_2 + 2p_3) + n_2(p_2 + 2p_3) + n_3 p_3 + p)/2p.$$

where $n_1$, $n_2$, $n_3$ are the number of cases in the three priority levels, $p_1$, $p_2$, $p_3$ are the number of positive cases, and p is the prevalence in the population.

To evaluate the uncertainty measures for identifying a high-confidence subset with higher performance, ROC metrics and RTAT were compared on the full test set to the 80% highest uncertainty measure cases. AUC differences were tested using DeLong's test for correlated ROC curves. Youden index and RTAT differences were tested using a bootstrap paired test for differences in means with 1,000 samples.

For hemorrhage detection, the ROC from seen centers and unseen centers were compared. The system yielded an ROC-AUC of 0.97 on data from seen centers and 0.95 on data from unseen centers. At the selected operating point, the system yielded a sensitivity/specificity of 0.92/0.93 on data from seen centers and 0.86/0.92 on data from unseen centers.

For hemorrhage segmentation, the total volume of acute hemorrhage estimated by automated and manual segmentations were compared for hemorrhages smaller and larger than 20 cm$^3$. 95% limits of agreement were 6 cm$^3$ for hemorrhages less than 20 cm$^3$ and 31 cm$^3$ for hemorrhages 20-456 cm$^3$.

For hemorrhage subtyping, the ROC from seen centers and unseen centers were compared. The system yielded an ROC-AUC for SAH/SDH/EDH/IPH/IVH of 0.90/0.92/0.93/0.92/0.96 on data from seen centers and 0.88/0.85/0.77/0.92/0.96 on data from unseen centers.

The performance-coverage curves for AUC, sensitivity, and specificity were generated. The calibrated-classifier uncertainty measure improved the Youden index (sensitivity+specificity−1) from 0.84 to 0.93 (p<0.001) excluding the 20% lowest confidence samples from seen centers, and from 0.78 to 0.88 (p<0.001) from unseen centers. The Dempster-Shafer uncertainty measure improved the index from 0.84 to 0.92 (p<0.001) from seen centers and from 0.78 to 0.89 (p<0.001) from unseen centers. The calibrated-classifier and Dempster-Shafer uncertainty measures improved the AUC from 0.972 to 0.986 and 0.985 on seen centers and from 0.945 to 0.963 and 0.962 excluding the 20% lowest confidence cases.

Performance-coverage curves for the three-way triage were generated. Using the calibrated-classifier uncertainty measure, triaging the 20% lowest confidence with an intermediate priority improved the simulated RTAT from 20% of baseline to 15% (p<0.001) from seen centers and from 26% to 20% (p<0.001) from unseen centers. Using the Dempster-Shafer uncertainty measure, it improved the simulated RTAT from 20% of baseline to 15% (p<0.001) from seen centers and from 26% to 19% (p<0.001) from unseen centers.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 4:
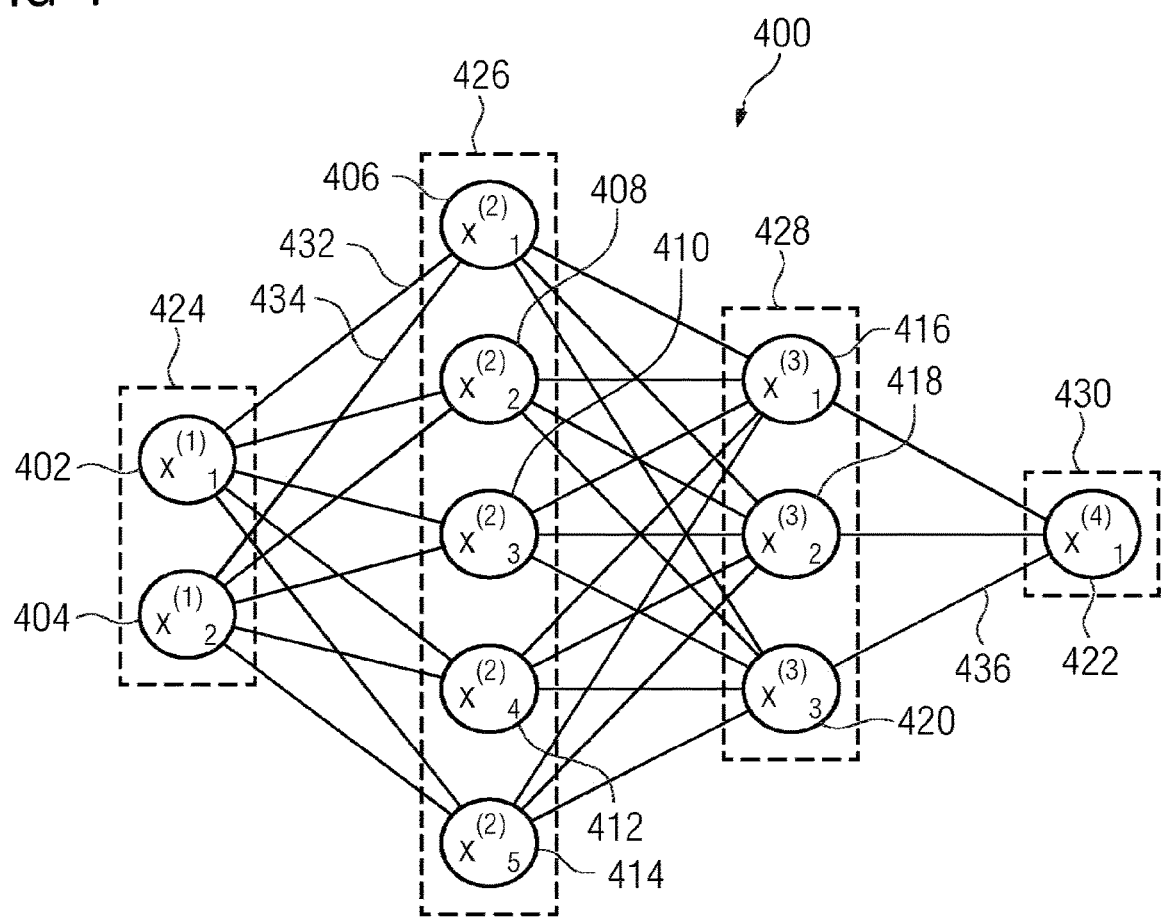
FIG. 4 shows an exemplary artificial neural network that may be used to implement one or more embodiments.

FIG. 4 shows an embodiment of an artificial neural network 400, in accordance with one or more embodiments. Alternative terms for "artificial neural network" are "neural network", "artificial neural net" or "neural net". Machine learning networks described herein, such as, e.g., the machine learning based network utilized at step 104 of FIG. 1 or the machine learning based network shown in FIG. 2 or 3, may be implemented using artificial neural network 400.

The artificial neural network 400 comprises nodes 402-422 and edges 432, 434, . . . , 436, wherein each edge 432, 434, . . . , 436 is a directed connection from a first node 402-422 to a second node 402-422. In general, the first node 402-422 and the second node 402-422 are different nodes 402-422, it is also possible that the first node 402-422 and the second node 402-422 are identical. For example, in FIG. 4, the edge 432 is a directed connection from the node 402 to the node 406, and the edge 434 is a directed connection from the node 404 to the node 406. An edge 432, 434, . . . , 436 from a first node 402-422 to a second node 402-422 is also denoted as "ingoing edge" for the second node 402-422 and as "outgoing edge" for the first node 402-422.

In this embodiment, the nodes 402-422 of the artificial neural network 400 can be arranged in layers 424-430, wherein the layers can comprise an intrinsic order introduced by the edges 432, 434, . . . , 436 between the nodes 402-422. In particular, edges 432, 434, . . . , 436 can exist only between neighboring layers of nodes. In the embodiment shown in FIG. 4, there is an input layer 424 comprising only nodes 402 and 404 without an incoming edge, an output layer 430 comprising only node 422 without outgoing edges, and hidden layers 426, 428 in-between the input layer 424 and the output layer 430. In general, the number of hidden layers 426, 428 can be chosen arbitrarily. The number of nodes 402 and 404 within the input layer 424 usually relates to the number of input values of the neural network 400, and the number of nodes 422 within the output layer 430 usually relates to the number of output values of the neural network 400.

In particular, a (real) number can be assigned as a value to every node 402-422 of the neural network 400. Here, $x^{(n)}_i$ denotes the value of the i-th node 402-422 of the n-th layer 424-430. The values of the nodes 402-422 of the input layer 424 are equivalent to the input values of the neural network 400, the value of the node 422 of the output layer 430 is equivalent to the output value of the neural network 400. Furthermore, each edge 432, 434, . . . , 436 can comprise a weight being a real number, in particular, the weight is a real number within the interval [−1, 1] or within the interval [0, 1]. Here, $w^{(m,n)}_{i,j}$ denotes the weight of the edge between the i-th node 402-422 of the m-th layer 424-430 and the j-th node 402-422 of the n-th layer 424-430. Furthermore, the abbreviation $w^{(n)}_{i,j}$ is defined for the weight $w^{(n,n+1)}_{i,j}$.

In particular, to calculate the output values of the neural network 400, the input values are propagated through the neural network. In particular, the values of the nodes 402-422 of the (n+1)-th layer 424-430 can be calculated based on the values of the nodes 402-422 of the n-th layer 424-430 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is primarily used to introduce non-linearities in the composite function and possibly for normalization purposes.

In particular, the values are propagated layer-wise through the neural network, wherein values of the input layer 424 are given by the input of the neural network 400, wherein values of the first hidden layer 426 can be calculated based on the values of the input layer 424 of the neural network, wherein values of the second hidden layer 428 can be calculated based in the values of the first hidden layer 426, etc.

In order to set the values $w^{(m,n)}_{i,j}$ for the edges, the neural network 400 has to be trained using training data. In particular, training data comprises training input data and training output data (denoted as $t_i$). For a training step, the neural network 400 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 400 (backpropagation algorithm). In particular, the weights are changed according to $$w'^{(n)}_{i,j} = w^{(n)}_{i,j} - \gamma \cdot \delta_j^{(n)} \cdot x_i^{(n)}$$

wherein γ is a learning rate, and the numbers $\delta^{(n)}_j$ can be recursively calculated as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)} = (x_k^{(n+1)} - t_j^{(n+1)}) \cdot f'(\Sigma_i x_i^{(n)} \cdot w_{i,j}^{(n)})$$

if the (n+1)-th layer is the output layer 430, wherein f' is the first derivative of the activation function, and $y^{(n+1)}_j$ is the comparison training value for the j-th node of the output layer 430.

Figure 5:
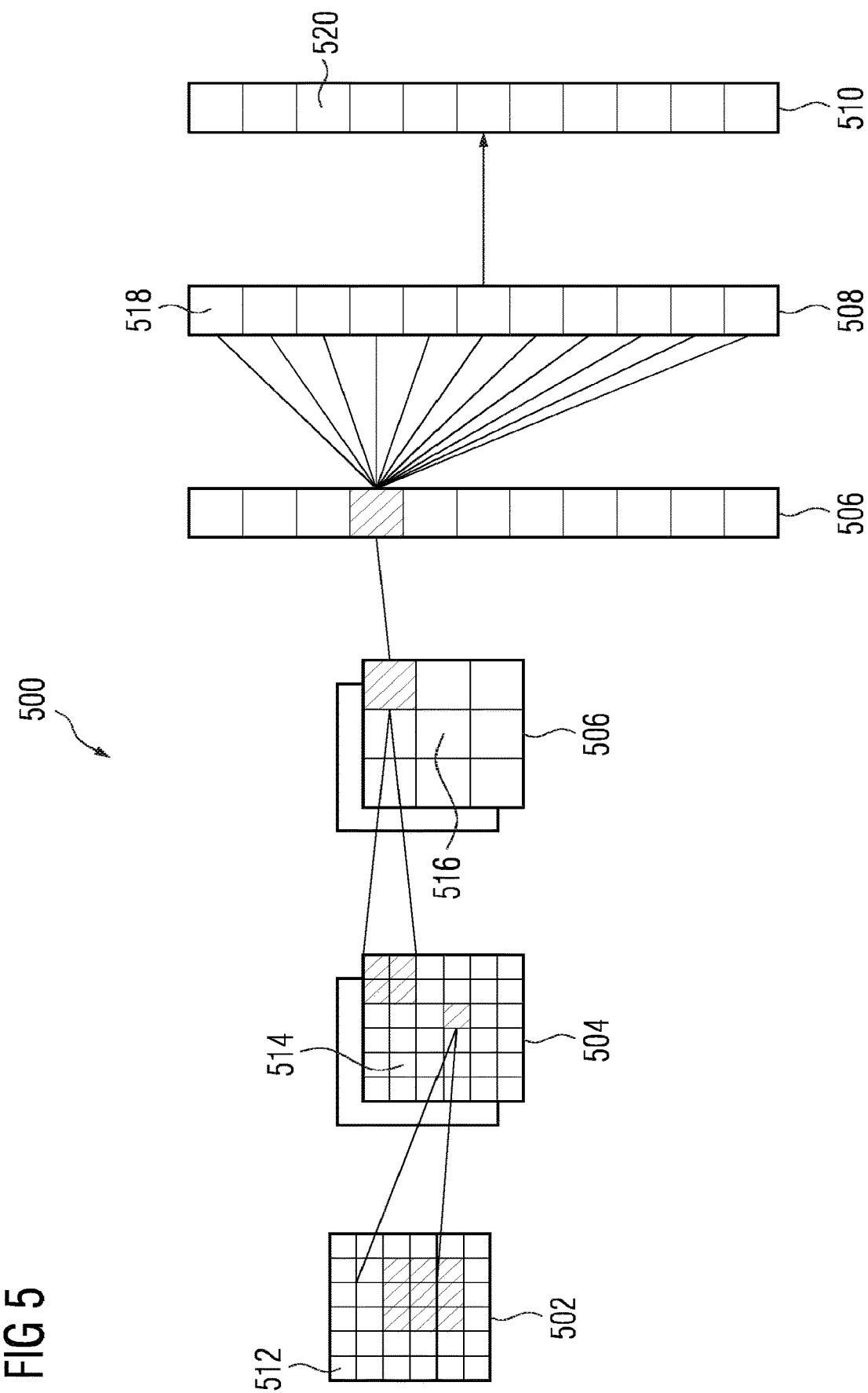
FIG. 5 shows a convolutional neural network that may be used to implement one or more embodiments.

FIG. 5 shows a convolutional neural network 500, in accordance with one or more embodiments. Machine learning networks described herein, such as, e.g., the machine learning based network utilized at step 104 of FIG. 1 or the machine learning based network shown in FIG. 2 or 3, may be implemented using convolutional neural network 500.

In the embodiment shown in FIG. 5, the convolutional neural network comprises 500 an input layer 502, a convolutional layer 504, a pooling layer 506, a fully connected layer 508, and an output layer 510. Alternatively, the convolutional neural network 500 can comprise several convolutional layers 504, several pooling layers 506, and several fully connected layers 508, as well as other types of layers. The order of the layers can be chosen arbitrarily, usually fully connected layers 508 are used as the last layers before the output layer 510.

In particular, within a convolutional neural network 500, the nodes 512-520 of one layer 502-510 can be considered to be arranged as a d-dimensional matrix or as a d-dimensional image. In particular, in the two-dimensional case the value of the node 512-520 indexed with i and j in the n-th layer 502-510 can be denoted as $x^{(n)}_{[i,j]}$. However, the arrangement of the nodes 512-520 of one layer 502-510 does not have an effect on the calculations executed within the convolutional neural network 500 as such, since these are given solely by the structure and the weights of the edges.

In particular, a convolutional layer 504 is characterized by the structure and the weights of the incoming edges forming a convolution operation based on a certain number of kernels. In particular, the structure and the weights of the incoming edges are chosen such that the values $x^{(n)}_k$ of the nodes 514 of the convolutional layer 504 are calculated as a convolution $x^{(n)}_k = K_k * x^{(n-1)}$ based on the values $x^{(n-1)}$ of the nodes 512 of the preceding layer 502, where the convolution * is defined in the two-dimensional case as $$x_k^{(n)}[i,j] = (K_k * x^{(n-1)})[i,j] = \Sigma_{i'} \Sigma_{j'} K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 512-518 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 512-520 in the respective layer 502-510. In particular, for a convolutional layer 504, the number of nodes 514 in the convolutional layer is equivalent to the number of nodes 512 in the preceding layer 502 multiplied with the number of kernels.

If the nodes 512 of the preceding layer 502 are arranged as a d-dimensional matrix, using a plurality of kernels can be interpreted as adding a further dimension (denoted as "depth" dimension), so that the nodes 514 of the convolutional layer 504 are arranged as a (d+1)-dimensional matrix. If the nodes 512 of the preceding layer 502 are already arranged as a (d+1)-dimensional matrix comprising a depth dimension, using a plurality of kernels can be interpreted as expanding along the depth dimension, so that the nodes 514 of the convolutional layer 504 are arranged also as a (d+1)-dimensional matrix, wherein the size of the (d+1)-dimensional matrix with respect to the depth dimension is by a factor of the number of kernels larger than in the preceding layer 502.

The advantage of using convolutional layers 504 is that spatially local correlation of the input data can exploited by enforcing a local connectivity pattern between nodes of adjacent layers, in particular by each node being connected to only a small region of the nodes of the preceding layer.

In embodiment shown in FIG. 5, the input layer 502 comprises 36 nodes 512, arranged as a two-dimensional 6×6 matrix. The convolutional layer 504 comprises 72 nodes 514, arranged as two two-dimensional 6×6 matrices, each of the two matrices being the result of a convolution of the values of the input layer with a kernel. Equivalently, the nodes 514 of the convolutional layer 504 can be interpreted as arranges as a three-dimensional 6×6×2 matrix, wherein the last dimension is the depth dimension.

A pooling layer 506 can be characterized by the structure and the weights of the incoming edges and the activation function of its nodes 516 forming a pooling operation based on a non-linear pooling function f. For example, in the two dimensional case the values $x^{(n)}$ of the nodes 516 of the pooling layer 506 can be calculated based on the values $x^{(n-1)}$ of the nodes 514 of the preceding layer 504 as $$x^{(n)}[i,j] = f(x^{(n-1)}[id_1, jd_2], \ldots, x^{(n-1)}[id_1+d_1-1, jd_2+d_2-1])$$

In other words, by using a pooling layer 506, the number of nodes 514, 516 can be reduced, by replacing a number d1·d2 of neighboring nodes 514 in the preceding layer 504 with a single node 516 being calculated as a function of the values of said number of neighboring nodes in the pooling layer. In particular, the pooling function f can be the max-function, the average or the L2-Norm. In particular, for a pooling layer 506 the weights of the incoming edges are fixed and are not modified by training.

The advantage of using a pooling layer 506 is that the number of nodes 514, 516 and the number of parameters is reduced. This leads to the amount of computation in the network being reduced and to a control of overfitting.

In the embodiment shown in FIG. 5, the pooling layer 506 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 508 can be characterized by the fact that a majority, in particular, all edges between nodes 516 of the previous layer 506 and the nodes 518 of the fully-connected layer 508 are present, and wherein the weight of each of the edges can be adjusted individually.

In this embodiment, the nodes 516 of the preceding layer 506 of the fully-connected layer 508 are displayed both as two-dimensional matrices, and additionally as non-related nodes (indicated as a line of nodes, wherein the number of nodes was reduced for a better presentability). In this embodiment, the number of nodes 518 in the fully connected layer 508 is equal to the number of nodes 516 in the preceding layer 506. Alternatively, the number of nodes 516, 518 can differ.

Furthermore, in this embodiment, the values of the nodes 520 of the output layer 510 are determined by applying the Softmax function onto the values of the nodes 518 of the preceding layer 508. By applying the Softmax function, the sum the values of all nodes 520 of the output layer 510 is 1, and all values of all nodes 520 of the output layer are real numbers between 0 and 1.

A convolutional neural network 500 can also comprise a ReLU (rectified linear units) layer, which is an activation layer with a non-linear transfer function. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 500 can be trained based on the backpropagation algorithm. For preventing overfitting, methods of regularization can be used, e.g. dropout of nodes 512-520, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1. Certain steps or functions of the methods and workflows described herein, including one or more of the steps or functions of FIG. 1, may be performed by a server or by another processor in a network-based cloud-computing system. Certain steps or functions of the methods and workflows described herein, including one or more of the steps of FIG. 1, may be performed by a client computer in a network-based cloud computing system. The steps or functions of the methods and workflows described herein, including one or more of the steps of FIG. 1, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 6:
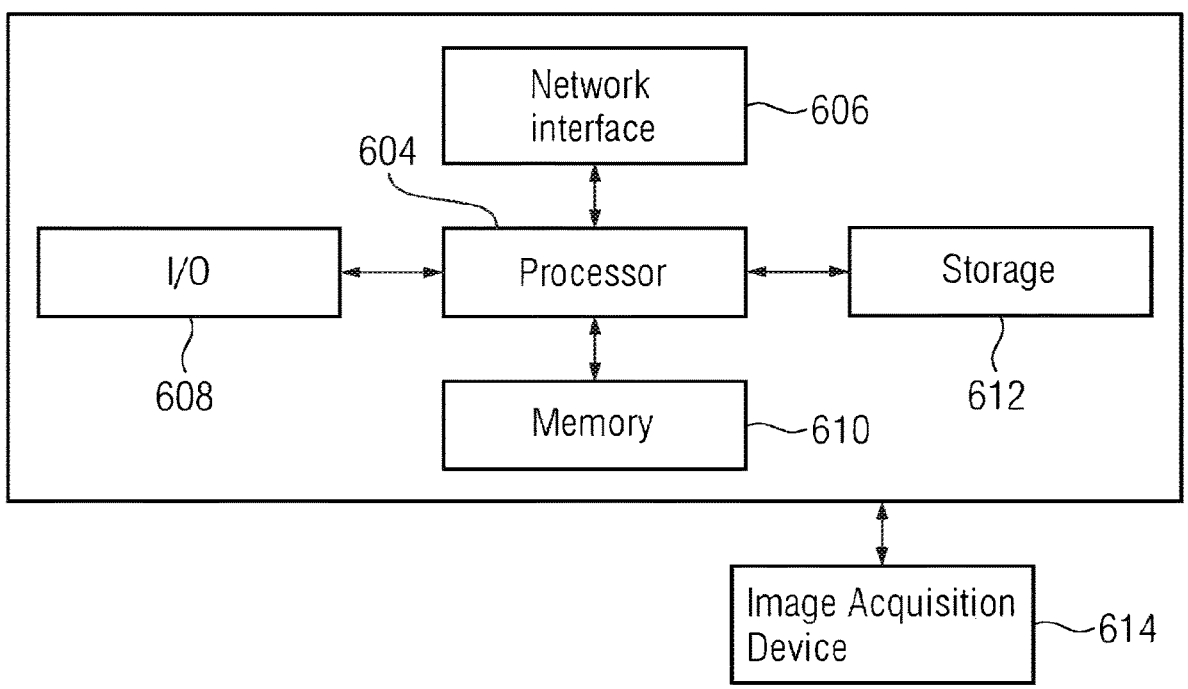
FIG. 6 shows a high-level block diagram of a computer that may be used to implement one or more embodiments.

A high-level block diagram of an example computer 602 that may be used to implement systems, apparatus, and methods described herein is depicted in FIG. 6. Computer 602 includes a processor 604 operatively coupled to a data storage device 612 and a memory 610. Processor 604 controls the overall operation of computer 602 by executing computer program instructions that define such operations. The computer program instructions may be stored in data storage device 612, or other computer readable medium, and loaded into memory 610 when execution of the computer program instructions is desired. Thus, the method and workflow steps or functions of FIG. 1 can be defined by the computer program instructions stored in memory 610 and/or data storage device 612 and controlled by processor 604 executing the computer program instructions. For example, the computer program instructions can be implemented as computer executable code programmed by one skilled in the art to perform the method and workflow steps or functions of FIG. 1. Accordingly, by executing the computer program instructions, the processor 604 executes the method and workflow steps or functions of FIG. 1. Computer 602 may also include one or more network interfaces 606 for communicating with other devices via a network. Computer 602 may also include one or more input/output devices 608 that enable user interaction with computer 602 (e.g., display, keyboard, mouse, speakers, buttons, etc.).

Processor 604 may include both general and special purpose microprocessors, and may be the sole processor or one of multiple processors of computer 602. Processor 604 may include one or more central processing units (CPUs), for example. Processor 604, data storage device 612, and/or memory 610 may include, be supplemented by, or incorporated in, one or more application-specific integrated circuits (ASICs) and/or one or more field programmable gate arrays (FPGAs).

Data storage device 612 and memory 610 each include a tangible non-transitory computer readable storage medium. Data storage device 612, and memory 610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 608 may include peripherals, such as a printer, scanner, display screen, etc. For example, input/output devices 608 may include a display device such as a cathode ray tube (CRT) or liquid crystal display (LCD) monitor for displaying information to the user, a keyboard, and a pointing device such as a mouse or a trackball by which the user can provide input to computer 602.

An image acquisition device 614 can be connected to the computer 602 to input image data (e.g., medical images) to the computer 602. It is possible to implement the image acquisition device 614 and the computer 602 as one device. It is also possible that the image acquisition device 614 and the computer 602 communicate wirelessly through a network. In a possible embodiment, the computer 602 can be located remotely with respect to the image acquisition device 614.

Any or all of the systems and apparatus discussed herein may be implemented using one or more computers such as computer 602.

One skilled in the art will recognize that an implementation of an actual computer or computer system may have other structures and may contain other components as well, and that FIG. 6 is a high-level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
receiving one or more input medical images of a patient;
performing a medical imaging analysis task from the one or more input medical images using a machine learning based network, the machine learning based network generating a probability score associated with the medical imaging analysis task;
determining an uncertainty measure representing an error associated with the probability score by:
selecting a calibration function comprising a fixed point defined according to a user selected threshold at which probability scores are totally uncertain;
applying the calibration function to the probability score, and
calculating an entropy of the probability score as the uncertainty measure based on results of the applied calibration function; and
making a clinical decision based on the probability score and the uncertainty measure.

2. The computer-implemented method of claim 1, wherein the medical imaging analysis task comprises at least one of detection, subtyping, or segmentation of an intracranial hemorrhage of the patient.

3. The computer-implemented method of claim 1, wherein making a clinical decision based on the probability score and the uncertainty measure comprises:
stratifying the patient into one of a plurality of patient groups based on the probability score and the uncertainty measure.

4. The computer-implemented method of claim 3, wherein the medical imaging analysis task comprises detection of an intracranial hemorrhage of the patient, and the plurality of patient groups comprises a high confidence positive detection patient group, a high confidence negative detection patient group, and a low confidence patient group.

5. The computer-implemented method of claim 1, wherein making a clinical decision based on the probability score and the uncertainty measure comprises:
determining whether to treat the patient based on the probability score and the uncertainty measure.

6. The computer-implemented method of claim 1, wherein making a clinical decision based on the probability score and the uncertainty measure comprises:
determining whether to perform a clinical test on the patient based on the probability score and the uncertainty measure.

7. The computer-implemented method of claim 1, wherein making a clinical decision based on the probability score and the uncertainty measure comprises:
prioritizing a worklist of a radiologist based on the probability score and the uncertainty measure.

8. An apparatus comprising:
means for receiving one or more input medical images of a patient;
means for performing a medical imaging analysis task from the one or more input medical images using a machine learning based network, the machine learning based network generating a probability score associated with the medical imaging analysis task;
means for determining an uncertainty measure representing an error associated with the probability score by:
selecting a calibration function comprising a fixed point defined according to a user selected threshold at which probability scores are totally uncertain;
applying the calibration function to the probability score, and
calculating an entropy of the probability score as the uncertainty measure based on results of the applied calibration function; and
means for making a clinical decision based on the probability score and the uncertainty measure.

9. The apparatus of claim 8, wherein the means for making a clinical decision based on the probability score and the uncertainty measure comprises:
means for stratifying the patient into one of a plurality of patient groups based on the probability score and the uncertainty measure.

10. The apparatus of claim 9, wherein the medical imaging analysis task comprises detection of an intracranial hemorrhage of the patient, and the plurality of patient groups comprises a high confidence positive detection patient group, a high confidence negative detection patient group, and a low confidence patient group.

11. A non-transitory computer readable medium storing computer program instructions, the computer program instructions when executed by a processor cause the processor to perform operations comprising:
receiving one or more input medical images of a patient;
performing a medical imaging analysis task from the one or more input medical images using a machine learning based network, the machine learning based network generating a probability score associated with the medical imaging analysis task;
determining an uncertainty measure representing an error associated with the probability score by:
selecting a calibration function comprising a fixed point defined according to a user selected threshold at which probability scores are totally uncertain;
applying the calibration function to the probability score, and
calculating an entropy of the probability score as the uncertainty measure based on results of the applied calibration function; and
making a clinical decision based on the probability score and the uncertainty measure.

12. The non-transitory computer readable medium of claim 11, wherein the medical imaging analysis task comprises at least one of detection, subtyping, or segmentation of an intracranial hemorrhage of the patient.

13. The non-transitory computer readable medium of claim 11, wherein making a clinical decision based on the probability score and the uncertainty measure comprises:
  determining whether to treat the patient based on the probability score and the uncertainty measure.

14. The non-transitory computer readable medium of claim 11, wherein making a clinical decision based on the probability score and the uncertainty measure comprises:
  determining whether to perform a clinical test on the patient based on the probability score and the uncertainty measure.

15. The non-transitory computer readable medium of claim 11, wherein making a clinical decision based on the probability score and the uncertainty measure comprises:
  prioritizing a worklist of a radiologist based on the probability score and the uncertainty measure.

* * * * *